United States Patent [19]

Langer et al.

[11] Patent Number: 4,812,724
[45] Date of Patent: Mar. 14, 1989

[54] INJECTOR CONTROL

[75] Inventors: Alois A. Langer, Forest Hills; Albert W. Rinne, Bethel Park, both of Pa.

[73] Assignee: Liebel-Flarsheim Corporation, Cincinnati, Ohio

[21] Appl. No.: 670,525

[22] Filed: Nov. 13, 1984

[51] Int. Cl.$^4$ .............................................. G05B 11/28
[52] U.S. Cl. .................................. 318/599; 318/468; 318/563; 318/603
[58] Field of Search ...................... 128/655, DIG. 1; 604/67, 65, 66, 155; 318/376, 599, 609, 610, 611, 615, 603, 327, 341, 318, 335, 302, 481, 563, 565, 564, 434, 466–467, 468; 361/168.1, 194, 186, 203; 307/442, 116, 123

[56] References Cited

U.S. PATENT DOCUMENTS

| | | | |
|---|---|---|---|
| 3,553,535 | 1/1971 | Weber | 361/194 |
| 3,596,111 | 7/1971 | Harr | 361/194 |
| 3,603,857 | 9/1971 | Crane | 318/302 |
| 3,611,092 | 10/1971 | Wilmunder | 318/302 |
| 3,623,474 | 11/1971 | Heilman | 128/655 |
| 3,628,101 | 12/1971 | Dietz | 361/194 |
| 3,631,847 | 1/1972 | Hobbs | 128/655 |
| 3,701,345 | 10/1972 | Heilman | 128/655 |
| 3,721,866 | 3/1973 | McIntosh | 361/194 |
| 3,731,679 | 5/1973 | Wilhelmson | 128/DIG. 1 |
| 3,736,930 | 6/1973 | Georgi | 604/67 |
| 3,864,608 | 2/1975 | Normile | 361/194 X |
| 4,006,736 | 2/1977 | Kranys | 128/655 |
| 4,230,977 | 10/1980 | Nelson | 318/302 |
| 4,311,949 | 4/1982 | Pelkmann | 318/341 |
| 4,328,800 | 5/1982 | Marx | 604/67 X |
| 4,422,619 | 12/1983 | Griffiths | 318/563 X |
| 4,435,173 | 3/1984 | Siposs | 604/155 |
| 4,449,082 | 5/1984 | Webster | 318/327 |
| 4,475,073 | 10/1984 | Hawkins | 318/609 |
| 4,475,666 | 10/1984 | Bilbrey | 604/155 X |
| 4,477,753 | 10/1984 | Rateel | 318/563 |
| 4,491,905 | 1/1985 | Arakawa | 318/563 |
| 4,501,531 | 2/1985 | Bilstad | 604/67 X |
| 4,529,401 | 7/1985 | Leslie | 604/67 |
| 4,697,221 | 9/1987 | Pasquarella | 361/194 |

Primary Examiner—Bentsu Ro
Attorney, Agent, or Firm—Wood, Herron & Evans

[57] ABSTRACT

A control system for an angiographic injector which precisely regulates the speed of a motor used to expel contrast media from a syringe. The control system is centered around a microprocessor which receives commands from the operator via a keyboard, and then regulates the speed of the motor by supplying drive command pulses to a circuit which integrates the difference in frequency between the command pulses and another pulse train whose frequency is proportional to actual motor speed. The control system also includes a velocity loop which uses the motor back EMF to supply an analog voltage also proportional to motor speed to a difference amplifier in a conventional velocity loop. The system is a dual loop controller where the second loop provides approximate speed control, while the first loop provides a "velocity correction" voltage required to bring the system to zero steady state speed error. Motor speed pulses are provided by an incremental encoder, the pulses from which are counted by the microprocessor to limit the volume of fluid injected. Various safety systems guard the injectors performance and help prevent over volume injections. These systems are part of the velocity control and are also disclosed.

6 Claims, 2 Drawing Sheets

FIG. 2
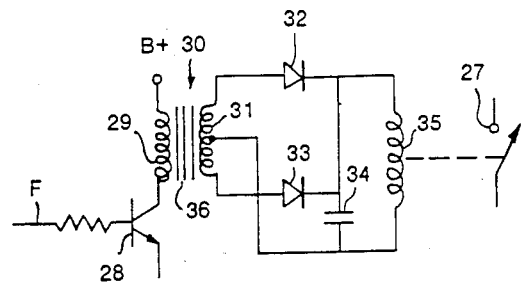
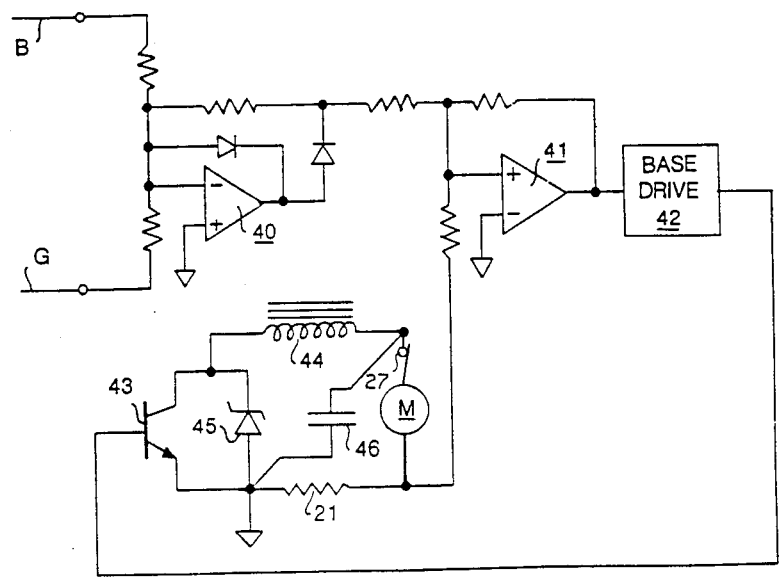
FIG. 3

INJECTOR CONTROL

BACKGROUND OF THE INVENTION

This application relates to the general field of angiography; which is the technique of studying the vascular system by means of X-rays while injecting a "contrast media," typically an iodine based fluid, into the blood vessel or organ to be studied. In order for this process to be maximally successful, the flow from the syringe must be precisely controlled and this control has been the subject of several patent applications. These systems have all exhibited various problems, most of which are eliminated by the system disclosed here. In U.S. Pat. Nos. 3,623,474 and 3,631,847 issued to Heilman et al and Hobbs respectively, a signal directly proportional to flow rate is fed back to produce a flow error signal used to control motor speed. The disadvantages of straight velocity control systems are discussed in Heilman's subsequent U.S. Pat. No. 3,701,345 and include mainly the problems in measuring motor velocity over a wide range. For example, the velocity feedback system originally disclosed included a tachometer which produced an analog feedback voltage. This feedback scheme is later described to drift and be subject to noise at low speeds. To solve this problem, in U.S. Pat. No. 3,701,345 a position feedback system is described. In such a system, a potentiometer is used to sense the position of the plunger. The position signal is compared to a command signal and the difference drives the motor. If the command is a ramp of constant slope, then the motor will move at nearly constant velocity. The position signal from the potentiometer is also used to limit the volume of fluid ejected from the syringe by comparing it to a known position command signal which represents the position at which the injector should stop.

Even this improved control system has its limitations, however. Since position is fed back, the system only guarantees that the average velocity between two positions is such that the plunger is in the right place at the end of a certain time interval. This means that velocity can increase and decrease around this average value as long as the average stays the same. From a control systems point of view, there is an extra integrator in the feedback loop and system stability is compromised. The implications to performance in angiography is that a position control system is not as resistant to factors which might cause velocity to briefly change. Such a factor which is quite significant, is imperfections in the ballscrew mechanism, which is typically used to convert the rotary motion of the motor to the linear motion required to move the plunger. The present injector is of significantly greater power than previous machines by almost a factor of two. The force on the ballscrew is doubled and a larger ballscrew has to be used. This means that the possibility for velocity variations due to ballscrew effects is increased. The inventive control system addresses this problem by controlling velocity directly and incorporates a velocity correction feedback path to maintain velocity control with great accuracy.

Angiographic injectors have typically employed a mechanical means for stopping the plunger in case of failure. Given the increased power of this system, such mechanical means would have to be extremely rugged, making the injector head very large and unwieldy. However, given the power of microprocessors for performing performance tests at extremely high speed, it is possible to design an injector with microprocessor control and eliminate any mechanical means for limiting plunger travel. Given the fact that many users do not use mechanical limits, the fact that they are subject to great stress and may in fact fail themselves and the impossibility to set them for each volume limit in a multi-bolus injection, the use of an "electronic stop" can in fact result in enhanced system reliability.

SUMMARY OF THE INVENTION

It is, therefore, an object of the present invention to provide a method for improved injection rate control in an angiographic injector, and in particular, a method yielding great system stability and being resistant to factors which may excite modes of short-term speed variations. Since a microprocessor is being used in the injector to enhance flexibility for injection parameter entry by the operator and to provide a means for sophisticated "electronic stop" volume limiting backup mechanisms, a further object of the invention is to provide a control system which is easily commanded by a microprocessor.

Microprocessors by their nature cannot directly control in an analog fashion such as has been the custom in the past. To be part of a system in an analog fashion with great precision requires a precise digital to analog converter, a very expensive and potentially unreliable component. Microprocessors are best suited to supplying some sort of pulse perhaps with the pulse interval representing the variable to be controlled. It is, therefore, an object of this invention to provide a velocity control system which is commanded by a computer's natural output, namely, a pulse train.

Computers have one potential drawback, however, and that is they are subject to "crashing." This means in general that the processor fails to execute its program in a controlled manner and, in fact, may be running useless code. A "crashed" computer may do unpredictable things, and it is an object of this invention to provide circuits which cause the motor not to run in case of microprocessor failure.

Preparing a patient for angiography is a significant procedure. A catheter is introduced into a peripheral artery or vein or other vascular element so the process is invasive. Should the injector fail, all the patient preparation might be in vain, so therefore it is an additional object of the invention to provide a self test feature so that it can be determined whether or not the machine is operational before it is asked to perform an injection. This self test feature is activated when the machine is turned on and is very thorough and extensive.

Basically, the present invention is an improvement over the prior art by employing dual loop control. One of the loops is very precise and is under direct control of the microcomputer. Plunger position is tracked by two independent measuring circuits, an incremental encoder and a potentiometer. Since volume is such a critical parameter, these are not arranged as a primary circuit and backup circuit but rather are constantly being simultaneously monitored by the computer. Both are measures of injected volume and must agree with each other in order for the injection to continue. Thus, both volume measuring circuits must be operational or else the machine stops. The incremental encoder is based on a wheel attached to the motor shaft and gives, say, 32 pulses per revolution of the motor. These pulses are counted by the computer and are used to limit the injection volume. The precision of this count is such that 0.1 ml volumes are possible, which is an accuracy heretofore unavailable in the injector field. In keeping with the philosophy of maximum redundancy on volume limiting, an additional circuit monitors the voltage from the potentiometer and asserts an error interrupt to the computer should the plunger somehow move too far forward in spite of the other volume limiting systems.

These and other aspects of the invention will become evident to those skilled in the art from an examination of the drawings and a description of the preferred embodiment.

BRIEF DESCRIPTION OF THE DRAWINGS

In FIGS. 2 and 3, additional blocks of the overall system are shown in greater detail.

DETAILED DESCRIPTION OF THE DRAWINGS

Figure 1:
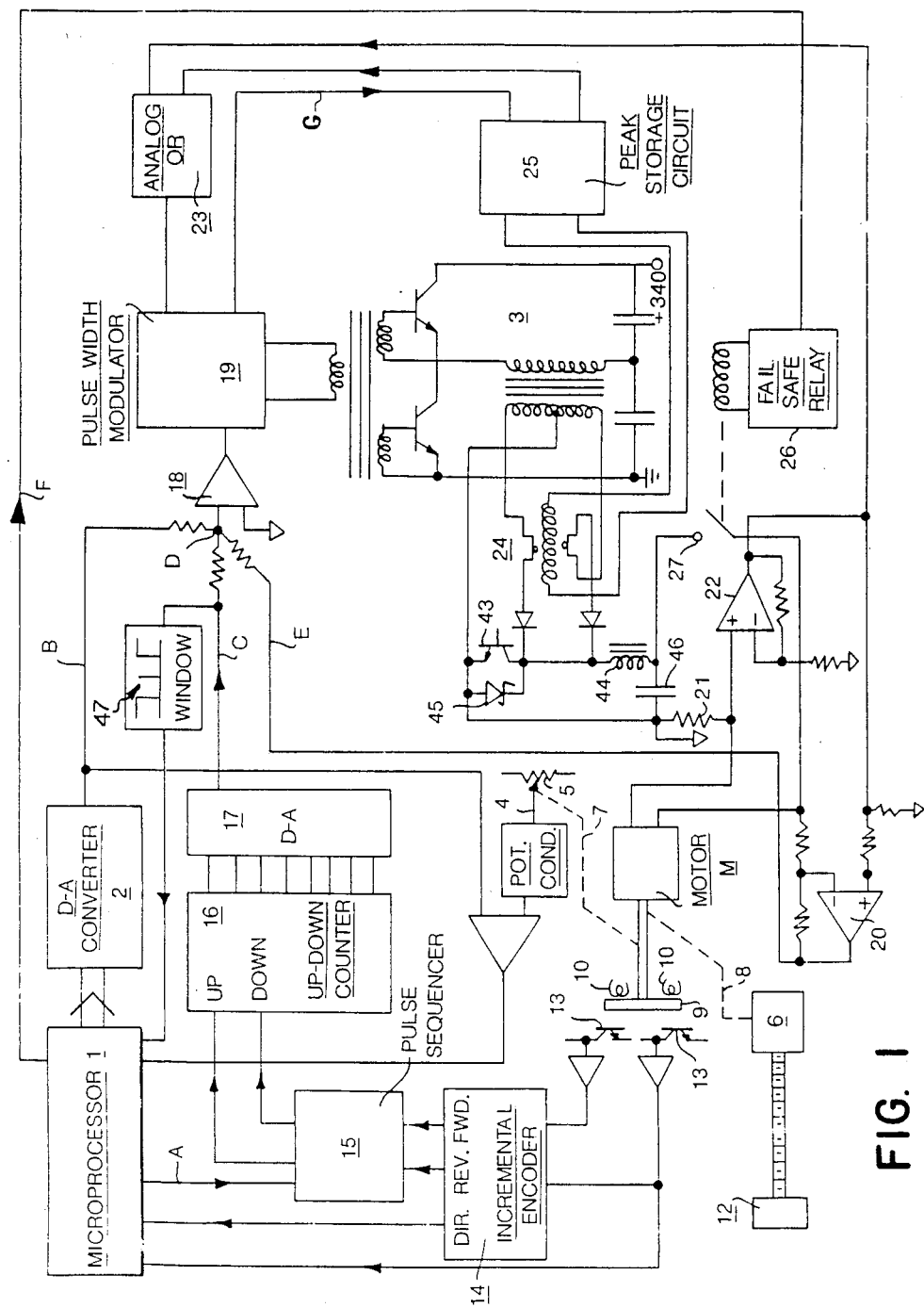
FIG. 1 shows a block diagram which is the overall system.

Considering the drawings in more detail, FIG. 1 is an overall view of the injector and its velocity control system. Central to the control is a microprocessor 1 which communicates to a removable console (not shown) via a serial link as is common to computer systems. By activating keys on the console, various parameters necessary to complete an injection can be entered by the user. The mode of entering this data on such a console is the subject of our commonly-assigned, co-pending application Ser. No. 670,685, entitled Improvements in Injectors and Injector Consoles, having the same filing date as the present application, now U.S. Pat. No. 4,650,465.

Upon receiving a valid flow rate command and a signal to start the injector, the microprocessor supplies a pulse train in line A whose frequency is directly proportional to the desired flow rate. The frequency can be very accurately controlled by known software methods and is derived from the quartz crystal clock of the processor. Quartz crystals are, of course, known for their frequency, accuracy and stability contributing to the accuracy of the flow command pulse train. At the same time, Microprocessor 1 sends an 8 bit flow command word to multichannel D-A converter 2. The resulting low precision analog voltage becomes the command for the velocity loop B. This need not be of high precision because of the velocity correction loop C which in effect "trims" the velocity loop as will be seen subsequently. Therefore, there are two variables which set the motor speed, the voltage from the DAC and the frequency of the pulse train.

At the other end of the control system is power amplifier 3 which supplies the high power necessary to drive the motor M, often in excess of 1000 watts. This is of conventional design and is a switching amplifier derived from the half bridge topology. The main components are illustrated, but will not be described in great detail herein.

The motor M drives the slider 4 of a potentiometer 5 and reduction gear 6 (the driving means being represented by dashed line ganging 7 and 8), and an encoder wheel 9. The encoder wheel interrupts light beams from two LED's 10, or the like, and the reduction gear drives a lead screw 11, which, when rotated, in turn advances a piston 12 along the length of the screw.

Except for the interruptions due to wheel 9, the LED light beams illuminate the light-sensitive transistors 13.

The interruptions result in pulses from each of the two channels being applied by the transistors which are approximately 90° out of phase to an incremental encoder circuit 14 having three outputs, shown as DIR., REV., and FWD. The encoder assigns directions significance to the pulses, i.e., whether they result from clockwise or anti-clockwise motor rotation, i.e., lead screw goes forward or reverse, so one of three outputs is for forward pulses, and another for reverse pulses. The third output is for direction. Total pulses are also sent to the processor 1, from one direct channel of the wheel, whereas the other two outputs are applied to the pulse sequencer 15, as are the pulses on line A from the processor 1. Total pulses are counted by the processor to limit volume.

The pulse sequencer itself is connected to up-down counter 16, causing the latter to count up both line A pulses and, reverse pulses from the incremental encoder. On the other hand, the sequencer makes the up-down counter count down forward pulses. At any given moment, the parallel output of the up-down counter has a word which represents the algebraic difference then existing between the net pulse output of the processor via line A, and the net pulse output of the interrupter wheel. This word is applied to D-A converter 17 which produces an analog signal which is algebraically summed at a terminal D with the flow command signal by amplifier 18 which applies the resultant signal to the pulse width modulator 19. Pulse width modulator 19 increases (or decreases the duty cycle of pulses fed by power amplifier 3 to the motor, thus varying the motor's power as is common in off line switching power supplies.

Via a conventional velocity loop E, an analog signal from an amplifier 20 representing motor current is summed at terminal D with the flow command and velocity correction signal. Motor voltage or back emf is roughly proportional to motor speed. Motor current flowing through a resistor 21 creates a voltage which is sensed by an amplifier 22, the output voltage of which is applied to amplifier 20 and to an analog OR circuit 23. A signal proportional to current is subtracted from motor voltage to compensate for motor armature resistance. An alternate measure of motor current is derived from a current-sensing transformer 24 by peak storage circuit 25, and the latter applies this measure as an analog voltage to the OR circuit, which in turn applies the larger of the current-derived voltage of amplifier 22 and the storage circuit voltage 25 to the modulator, thereby limiting the injection pressure.

At any instant from the time of the pulse train's beginning on line A, the pulse total represents how much liquid should have been injected by that time. At the same time, the net of forward and reverse pulses from the decoder represents the actual amount injected since the motor began to rotate the wheel 9. Therefore, any non-zero output of the up-down counter is the measure of an error in injected amount, and by summing that non-zero output with the flow command, the latter is increased or decreased, as needed, to compensate for the injection error.

Preferably, the processor also monitors volume error by comparing the piston-position proportional voltage at potentiometer 5 and an absolute volume limit command signal from another channel of the D-A converter, and shuts the motor M off should an intolerable discrepancy develop.

As suggested elsewhere above, a number of conditions can occur which call for stopping the injector for the good of the patient. However, it has also been noted that the motor is rather powerful, so stopping it can be a problem. In the present injector, the motor stops in response to proportional braking, a technique which optimizes the application of braking effect to the motor.

Also, under some circumstances it is desired to ramp the flow command downward, i.e., decrease motor speed steadily, and not abruptly, but nevertheless rather markedly. In the prior art, while the pressure in the cartridge aids the ramp process to some extent, the motor nevertheless tends to coast due to armature inertia, i.e., to resist being slowed down so to speak. The duty cycle control of the motor acts by decreasing the energization of the motor, but cannot reverse it.

According to the invention, we provide for ramping the motor by means of braking the motor's speed in proportion to the desired rate of decrease, as represented by decreasing the flow command in accordance with the desired downward ramp slope.

When motor M is not being supplied with driving current, it is coasting and therefore being a generator. Thus, in FIG. 3, the flow command positive voltage on line B is applied to the negatibve terminal of amplifier 40, where it is summed with a motor parameter negative voltage from line G. The latter voltage which may be from, say, line E, FIG. 1, but in any event is from a point in FIG. 1 where there is a motor current representative voltage, represents actual flow, so if the motor's speed is greater than its command, amplifier 40 will produce a flow difference positive output voltage which will turn on amplifier 41 which has its positive terminal connected to both the flow difference voltage and to the motor current representing voltage at the connection of resistor 21 to motor M and turns on base drive circuit 42 for transistor 43. At this time, if the power amplifier 3 is off, it effectively does not exist, and what the motor sees is a short circuit at transistor 43. As the motor is coasting at this point, it is acting as a generator loaded by the transistor to the extent base drive circuit 42 permits. At the same time, current through the inductor 44 and motor increases in linear fashion due to their inductance, and the voltage applied by resistor 21 to amplifier 41 becomes negative and turns the amplifier 41 off. During the flyback period of the inductor, while current flows through zener clamp 45, the motor current decreases, eventually turning on amplifier 41 again.

The above described cycle repeats and as the flow command is decreasing, energy will be transferred from the motor to the zener at the rate required to slow the motor.

A fail safe relay is provided to open contact 27, should the processor pulse output on line F fail. Thus, as shown in FIG. 2, the pulses are applied via line F to the base of a transistor 28, whereby to turn the transistor on and off at the pulse frequency. When the transistor is on there is a current due to D.C. supply voltage at a B+ terminal. This current passes through winding 29 of a transformer 30 also having a tapped winding 31, at the ends of which are diodes 32 and 33. The anodes of the diodes are connected together to one side of capacitor 34 and to one end of relay operating coil 35 which when energized closes contact 27, the other end of the coil 35 being connected to the other side of the capacitor and to the tap on winding 31. The transformer 30 has a core 36 which is constructed so as to store as much energy therein as is coupled through it when the transistor 28 is turned on by a pulse from line F. The energy storage capacity of the core is a function mainly of the size of an air gap in the core and the number of turns, and by appropriately proportioning these parameters it is possible to make the energy stored in the core substantially equal to that transformed through it when the transistor 28 is pulsed on.

Since the motor is driven by the current in the loop containing contact 27, this contact must be closed for the motor to turn. Due to the "flyback" effect, current flows substantially continuously through coil 35, i.e., when the transistor turns off between pulses, the energy stored in core 36 provides current in coil 35.

We claim:

1. An injector having a piston and a motor for positioning said piston; said injector also having a flow command signal producing means for producing a flow command signal, a motor control means, and a first pulse producing means for producing a first pulse train of frequency proportional to said flow command signal;
   said motor control means being connected to said flow command signal producing means and to said motor for receiving said flow command signal and driving said motor at a rate proportional to the flow rate commanded by said flow command signal, said motor when so driven providing a motor rate feedback signal corresponding to the actual rate at which it is being driven by said motor control means, to position said piston;
   said injector also having a second pulse producing means operated by said motor for producing a second pulse train having a frequency proportional to the actual rate at which said motor is positioning said piston, and an integrating means responsive to both said pulse trains for integrating the difference between the frequencies of said pulse trains and thereby producing a rate correction signal;
   said rate correction signal, said flow command signal and said motor rate feedback signal being applied to said motor control means such as to cause said motor to position said piston accurately.

2. The injector of claim 1 wherein said motor is an electric motor and produces a back emf corresponding to its rotation rate, and said back emf provides said motor rate feedback signal.

3. The injector of claim 2 wherein said injector includes proportional braking means connected to said motor for electrically loading said motor in proportional to a desired rate of decreasing when a calling for the motor rotation rate is less than the actual rate.

4. The injector of claim 3 wherein said motor control means includes an electric power amplifier for providing said motor with pulses whose duty cycle determine the rate of rotation of said motor and the extent to which said motor is loaded by said proportional braking means; said motor control means causing said pulses to have a duty cycle representative of said flow command signal as modified by said motor rate feedback signal and said rate correction signal.

5. The method of controlling an electric motor to drive an injector such as to inject a predetermined quantity of material in a predetermined time interval, comprising, at the beginning of said time interval;
   (1) applying electrical power to said motor at a level which, if maintained from the beginning of said time interval until the end thereof, would cause just said quantity to be injected during said time interval;

(2) applying a first stream of pulses to an integrating means, the rate at which said pulses are so applied being set independently of said motor but being dependent on a desired injection rate;

(3) applying a second stream of pulses to said integrating means, the rate at which said pulses are so applied being set by said motor at a rate varying in proportion to the speed of said motor;

said motor being of the type which produces a back emf proportional to its speed, and said integrating means being of the type which, at any given instant in said time interval, produces a difference signal representing a net difference between the total, in said time interval and till that given instant, of said first stream pulses and the corresponding total of said second stream pulses;

(4) modifying the application of said electrical power to said motor by means of a feedback signal which is representative of both said back emf and said difference signal, whereby to regulate the speed of said motor more accurately.

6. An injector system having a pulse-commanded motor, a source of command pulses and a motor control means connected in a circuit with said motor for driving said motor as a function of said pulses, including an open contact in said circuit which must be kept closed in order for said motor to be driven; said system also having a fail safe means connected to said source of command pulses and responsive to said pulses for keeping said contact closed solely while said pulses occur; said fail safe means including a relay for keeping said contact closed when driven by a DC source and a relay driver means;

said relay driver means comprising a transformer having a first winding for receiving said command pulses, a second winding, and a core coupling said windings, said core being constructed and arranged to return to said second winding substantially all the energy stored therein in response to termination of a pulse of current in said first winding; said relay driver means further comprising a steering diode means for causing current in said second winding due to said pulses, and current in said second winding due to said stored energy, to have the same sense; said relay being connected across said second winding, whereby pulsing said first winding will cause said relay to be substantially continuously energized by said DC source for keeping said contact closed when said first winding receives said command pulses;

a relay solenoid of said relay for keeping said contact closed, said relay solenoid connected across said second winding, said steering diode means being first and second diodes, said first diode interconnecting one end of said second winding and one end of said solenoid, the other end of said solenoid and an intermediate point on said second winding being directly connected together; said second diode interconnecting the one end of said second winding with the junction of said first diode and said one end of said solenoid, and also including a capacitor interconnected between the ends of said solenoids.

* * * * *

UNITED STATES PATENT AND TRADEMARK OFFICE
CERTIFICATE OF CORRECTION

PATENT NO. : 4,812,724

DATED : March 14, 1989

INVENTOR(S) : Langer et al.

It is certified that error appears in the above-identified patent and that said Letters Patent is hereby corrected as shown below:

Col. 2, lines 43-52 should be deleted.

Col. 4, line 31, after "decreases", add --)--.

Col. 5, line 25, "negatibve" should be --negative--.

Signed and Sealed this

Twelfth Day of June, 1990

Attest:

HARRY F. MANBECK, JR.

*Attesting Officer*   *Commissioner of Patents and Trademarks*